United States Patent [19]

Jackson et al.

[11] 4,357,939
[45] Nov. 9, 1982

[54] SANITARY NAPKIN WITH CROSS DIRECTIONAL FLUID DIRECTING MEANS

[75] Inventors: David M. Jackson; Robert J. Roeder, both of Appleton, Wis.

[73] Assignee: Kimberly-Clark Corporation, Neenah, Wis.

[21] Appl. No.: 219,946

[22] Filed: Dec. 24, 1980

[51] Int. Cl.³ .............................................. A61F 13/16
[52] U.S. Cl. ............................................... 128/290 R
[58] Field of Search ...................... 128/284, 287, 290 R

[56] References Cited

U.S. PATENT DOCUMENTS

| | | | |
|---|---|---|---|
| 2,960,089 | 11/1960 | Harwood et al. | 128/290 R |
| 3,036,573 | 5/1962 | Voigtman et al. | 128/290 R |
| 3,124,135 | 3/1964 | Olson | 128/290 R |
| 3,294,091 | 12/1966 | Morse | 128/290 R |
| 3,542,028 | 11/1970 | Beebe et al. | 128/290 R |
| 3,865,112 | 11/1975 | Roeder | 128/290 R |

Primary Examiner—C. Fred Rosenbaum
Attorney, Agent, or Firm—Howard Olevsky; William D. Herrick

[57] ABSTRACT

A sanitary napkin having a fluid directing means around an absorbent layer is provided. The napkin has a fluid impervious baffle covering the undersurface, extending up the sides and terminating along the longitudinal periphery of either side of the top surface of the layer. In a particularly preferred embodiment, two absorbent batts are utilized and fluid directional means are provided to direct the fluid in a cross direction extending under the longitudinal top covering portions of the baffle along the sides of the topmost layer and terminating between the bottom surface of the upper layer and the top surface of the lower layer.

5 Claims, 3 Drawing Figures

SANITARY NAPKIN WITH CROSS DIRECTIONAL FLUID DIRECTING MEANS

FIELD OF THE INVENTION

This invention relates to the field of sanitary napkins and particularly to a sanitary napkin having increased absorbent capacity.

BACKGROUND OF THE INVENTION

Sanitary napkins are generally comprised of at least two elements i.e. a fluid absorbing batt or layer and a fluid impermeable baffle to protect the undergarment of the wearer from leakage and/or fluid runoff from the absorbent batt. One of the problems associated with the design of the sanitary napkin is that a substantial portion of the absorbent material is not utilized due to the inability of the fluid to rapidly disperse through the absorbent matrix before local saturation of the absorbent material is complete. Also, during periods of high rates of flow, the fluid may be conducted along the surface of the absorbent material and/or a covering material placed over the absorbent component (the fluid pervious covering material used to maintain the integrity of the napkin) producing side leakage along the longitudinal edges of the napkin. The problems of localized saturation and side leakage have been treated independently in the past.

U.S. Pat. Nos. 3,294,091 and 4,200,103 disclosed the concept of extending the fluid impervious baffle up the sides of the absorbent batt and over the top surface of the napkin along each of the longitudinal edges thereof. The extension of the baffle onto the top surface of the absorbent component does seem to act to prevent side staining as long as a fluid barrier seal between the baffle and the cover material is maintained.

Conventional approaches to promotion of more even fluid distribution have been directed towards embossment patterns extending longitudinally along the length of the napkin. The theory behind the longitudinal embossment patterns is that the fluid would follow the embossment pattern lines which would tend to utilize the area between the surface of initial fluid contact and the edges of the napkin. Another approach to fluid distribution is disclosed in U.S. Pat. No. 3,230,955 which also provides for fluid distribution in the longitudinal direction but the distribution is accomplished by utilizing cellulose wadding material which had been laid in the machine direction producing fibers extending along the longitudinal direction. This tissue-like cover material when laid in the so-called machine direction, accomplished the same purpose as the longitudinal embossment lines.

Previously it has been thought necessary to convey fluid longitudinally to achieve enhanced absorbent utilization even though the fluid has a tendency to flow in all directions uniformly.

Another difficulty associated with the longitudinal directing of fluid is that, due to the nature of conventional cellulosic absorbent material used in napkins, very little of the bottom portion of the absorbent material is utilized. This is true because the top portion tends to become saturated and, as a result, discarded before the fluid migrates to the bottom portion of the absorbent batt. The sanitary napkin according to the teachings of this invention obtains superior absorbent capacity with superior fluid distribution while minimizing side staining.

SUMMARY OF THE INVENTION

According to this invention a sanitary napkin is provided with a fluid impermeable baffle covering the bottom of an absorbent layer, extending along the sides of the absorbent layer and longitudinally slightly over the surface of the absorbent facing the wearer i.e. the top surface.

In addition, the napkin of this invention is provided with a fluid directing means across the width of the top of the napkin overlaying the top surface of absorbent.

In fact, it is the particular combination of features which produces a superior result both from the standpoint of resistance to leakage and increased absorbent capacity. Neither the extended baffle nor the cross direction fluid directing means alone produce the superior results obtained when the cross direction means are utilized.

An especially preferred variation of this invention employs two absorbent layers with the flow directing means extending between the adjacent surfaces of the layers. This particular configuration produces a napkin with even greater absorbent utilization than that having flow directing means and one absorbent layer.

The subject invention can be more readily understood by reference to the drawings in which FIG. 1 is a diagrammatic plan view partially in cross section of one of the embodiments of the subject invention.

Figure 1:
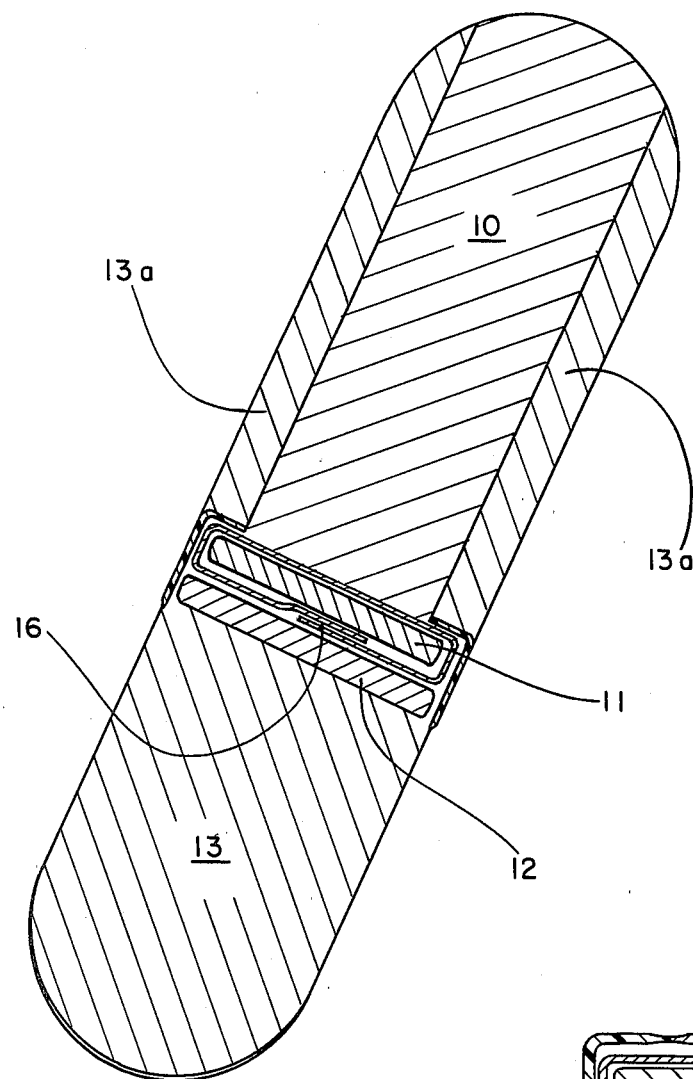
Figure 2:
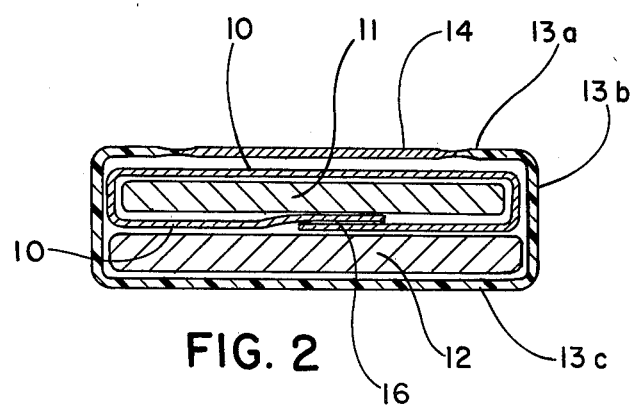
FIG. 2 is a diagrammatic cross section of a second embodiment.

As shown in FIGS. 1 and 2, a sanitary napkin having separate absorbent batts 11 and 12 are separated by cross direction tissue wadding 10 which completely encircles the uppermost absorbent batt 11 and is joined adhesively at overlap 16. The presently preferred configuration of the tissue wadding is for complete coverage of the bottom surface of the top absorbent batt although any coverage of the bottom surface is productively flow directive and sealing of the wadding can be accomplished directly to the bottom surface. Fluid impervious baffle 13 extends along and covers the bottom surface of the second absorbent batt 12 to form surface 13(c) and continuously extends upward along the sides of the sanitary napkin surrounding the sides of the absorbent batts and the sides of the fluid flow directing layer 10 at 13(b). The baffle extends partially across the top surface of the napkin at layer 13(a). The embodiment at FIG. 2 utilizes a cover material 14 which is preferably large pored and which is attached to the baffle material at the upper side face 13(a). Attachment as shown is by fusing with the cover material being thermoplastic, although adhesive attachment is possible.

Figure 3:
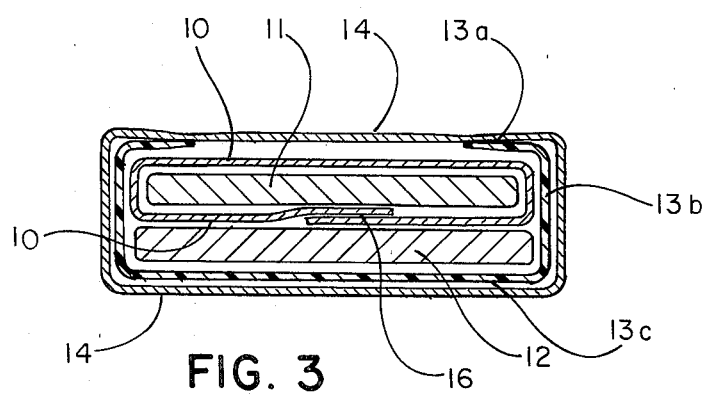
FIG. 3 is a third embodiment of the napkin of this invention.

FIG. 3 shows another embodiment which is identical to FIG. 2 in every respect except that the fluid pervious cover material was used as a wrap which completely encircles the other elements of the napkin. Such a material is sometimes utilized for purposes of comfort for the wearer.

The embodiment as shown in FIG. 1 does not include a specific separate cover material but if only a directional wadding is employed as the flow direction means the addition of a separate cover element is preferred for purposes of increased product integrity and strength. It is, of course, possible to combine the functions of the cover material and flow direction means as is shown in the embodiment in FIG. 1. In this instance a covering material could be rendered preferentially wettable by surfactant treatment extending in strips outward from the width of the napkin.

If a separate inexpensive flow directional means such as cross directional wadding is employed, either of the embodiments shown at FIGS. 2 and 3 are preferred.

Due to the increased efficiency of the napkin of this invention, napkins of reduced size having increased capacity are possible. These advantages are inherent in the napkin having only a single absorbent layer but to a more limited extent than the presently preferred embodiments having two absorbent layers. The three embodiments illustrated in the Figures can, of course, also be made with a single absorbent layer with the characteristics described for each of these embodiments also applying in those instances.

What is claimed is:

1. A sanitary napkin comprising in combination:
   (a) an absorbent component having a first batt proximal to the wearer and a second absorbent batt adjacent to the first batt and distal from the wearer;
   (b) a fluid impervious baffle overlaying the bottom surface of the second batt, the sides of the absorbent component and longitudinally extending peripheral segments of the surface of the first batt adjacent the wearer; and
   (c) a flow directional means extending over the surface of the first batt adjacent the wearer, under the edges of the longitudinal segments of the baffle, extending downward along the sides of the first batt and between the bottom surface of the first batt and the adjacent surface of the second batt, said means preferentially directing the flow across the width of the napkin.

2. The napkin of claim 1 wherein the flow directional means consist essentially of cross directional laid creped wadding.

3. The napkin of claims 1 or 2 wherein a fluid pervious cover overlays the fluid directing means.

4. The napkin of claims 1 or 2 wherein a fluid pervious cover overlays the fluid directing means and is fused to the longitudinally extending edges of the baffle.

5. The napkin of claim 1 wherein the flow directional means consists essentially of creped wadding.

* * * * *